United States Patent
Guyot et al.

(10) Patent No.: US 6,951,442 B1
(45) Date of Patent: Oct. 4, 2005

(54) DEVICE FOR INSPECTING, SAMPLING OR EXTRACTING AT A PRECISE SPOT BENEATH A SLAB

(75) Inventors: Jean-Luc Guyot, Gif sur Yvette (FR); Bruno Julienne, Montrouge (FR); Daniel Kerlau, Chatenay Malabry (FR); Marc Schiavi, Igny (FR)

(73) Assignee: Compagnie Generale des Matieres Nucleaires, Velizy-Villacoublay (FR)

( * ) Notice: Subject to any disclaimer, the term of this patent is extended or adjusted under 35 U.S.C. 154(b) by 0 days.

(21) Appl. No.: 09/623,604

(22) PCT Filed: Mar. 4, 1999

(86) PCT No.: PCT/FR99/00492

§ 371 (c)(1),
(2), (4) Date: Sep. 25, 2000

(87) PCT Pub. No.: WO99/45359

PCT Pub. Date: Sep. 10, 1999

(30) Foreign Application Priority Data

Mar. 5, 1998 (FR) .................................. 98 02702

(51) Int. Cl.⁷ ........................................... B02C 23/36
(52) U.S. Cl. ................... 414/308; 414/313; 254/395; 254/413
(58) Field of Search ................. 414/304, 305, 414/308, 313; 254/389, 394, 395, 413

(56) References Cited

U.S. PATENT DOCUMENTS

| | | | |
|---|---|---|---|
| 4,049,357 A | | 9/1977 | Hamisch, Jr. |
| 4,289,437 A | | 9/1981 | Hansen |
| 4,465,418 A | | 8/1984 | Norton |
| 4,663,114 A | * | 5/1987 | Cransac et al. ............. 376/271 |
| 4,836,125 A | | 6/1989 | Ballantyne et al. |
| 5,223,280 A | * | 6/1993 | Ogata et al. ............ 425/436 R |
| 5,379,657 A | | 1/1995 | Hasselman et al. |
| 5,526,989 A | * | 6/1996 | Staples et al. ................. 241/25 |

FOREIGN PATENT DOCUMENTS

| | | |
|---|---|---|
| DE | 34 15 299 A | 10/1985 |
| DE | 35 24 857 A | 1/1987 |
| DE | 36 13 038 A | 10/1987 |

* cited by examiner

Primary Examiner—Eileen D. Lillis
Assistant Examiner—Charles A. Fox
(74) Attorney, Agent, or Firm—Pearne & Gordon LLP (57) ABSTRACT

A tool (7) for sampling or extracting the contents of a pit (4) is suspended from a cable (8) passing through a narrow opening (3) in a slab (2) covering the pit. A crosspiece (13) hooked to guide cables (11) which converge on it makes it possible to displace the lifting cable (8) under the slab (2) according to different movements imposed by winches (10). Thus it is possible to move the tool (7) to the desired point with great precision and without having to descend into the pit (4).

17 Claims, 7 Drawing Sheets

DEVICE FOR INSPECTING, SAMPLING OR EXTRACTING AT A PRECISE SPOT BENEATH A SLAB

BACKGROUND OF THE INVENTION

The present invention relates to a device for examination, sampling or extraction at a precise point under a slab, and can be applied in particular to dangerous products emptied for long-term storage in silos whose ceiling is formed by a protective cover-slab pierced by a single opening, generally in the centre, and normally closed.

When a sampling or examination of a sample of the contents of the silo is decided, in the present state of the art it is normal to lower an appropriate mechanism suspended from a support cable into the silo through the opening. The mechanism can be a grab in the case of solid samples or an agitating and pumping unit for liquid or loose samples. But thus it is only possible to make samplings or examinations easily in a vertical direction from the opening. In order to proceed elsewhere, the end of the cable is pushed aside guiding it by rods engaged obliquely through the opening, which is time-consuming, not very precise, can present dangers and in general does not allow access to the edges of the silo whose width is often about ten meters.

SUMMARY OF THE INVENTION

The device according to the invention has the aim of making up for these defects and in particular to make it possible to carry out examinations or samplings of the contents of the silo easily at any point whatsoever, and to guide the mechanism lowered under the slab with great precision. The device according to the invention also has other advantages in that it does not require any human intervention under the slab or near the opening, and in that it is sufficiently sturdy not to need anything but infrequent maintenance, which is essential for the principal application envisaged concerning radioactive waste. It is characterised in that it comprises at least three guide cables situated under the slab, converging onto a guide means with hollowed out periphery, in the form of a cross or a star, located under the slab, to which they are attached crossing the slab by drilled holes located at the edge of the silo, and rolled onto winches operated by motors, a common control system for the winches, and in that the crosspiece is provided with surfaces for sliding the support cable between the attachment points and the guide cables.

Thus, the rolling up of the guide cables, each of them controlled independently by the control system, makes it possible to displace the crosspiece, as well as the support cable, which has previously been left hanging against a suitable face of the crosspiece between two anchor points of the guide cables. The examination or sampling mechanism is then pulled above the desired position, and then it suffices to lower it so that it arrives over the sample. Advantageously there can be four guide cables, the drill holes by which they pass under the slab being arranged in a rectangle, at the corners of silos of this same shape, which makes it possible to move the crosspiece anywhere under the slab.

The invention can be perfected in many other ways. Some have the objective of guaranteeing the precision of the displacement of the crosspiece. The winch motors can then be equipped with sensors measuring force, linked up to the control system, in order to evaluate the lengthening of the cables due to the traction and in consequence to rectify the motor commands; the drill holes can be equipped with sleeves carrying rollers defining a curved guiding device, in which a respective guide cable slides and which serves to orient it better towards the crosspiece by making the sleeve pivot using a motor directed by the control system. Finally, the winches can comprise drums with a hollowed surface with a helicoidal reception groove for the guide cables to be rolled in a single layer, which means that the rotation of the drums always unrolls the same length of guide cable.

Preferably the support cable is not submitted to excessive friction. Thus the crosspiece, the opening of the slab or both can be provided with rollers on which the cable slides. Precise guidance of the support cable is obtained if the surfaces of the crosspiece are concave when linking the hooking points of the guide cable, the sliding rollers arranged around the opening of the slab being arranged on a polygonal and turning crown.

One embodiment of the invention, given as a purely illustrative example, will be described with the help of the following figures and will make it easier to understand its characteristics, aims and advantages.

DESCRIPTION OF EXAMPLE EMBODIMENTS

Figure 1:
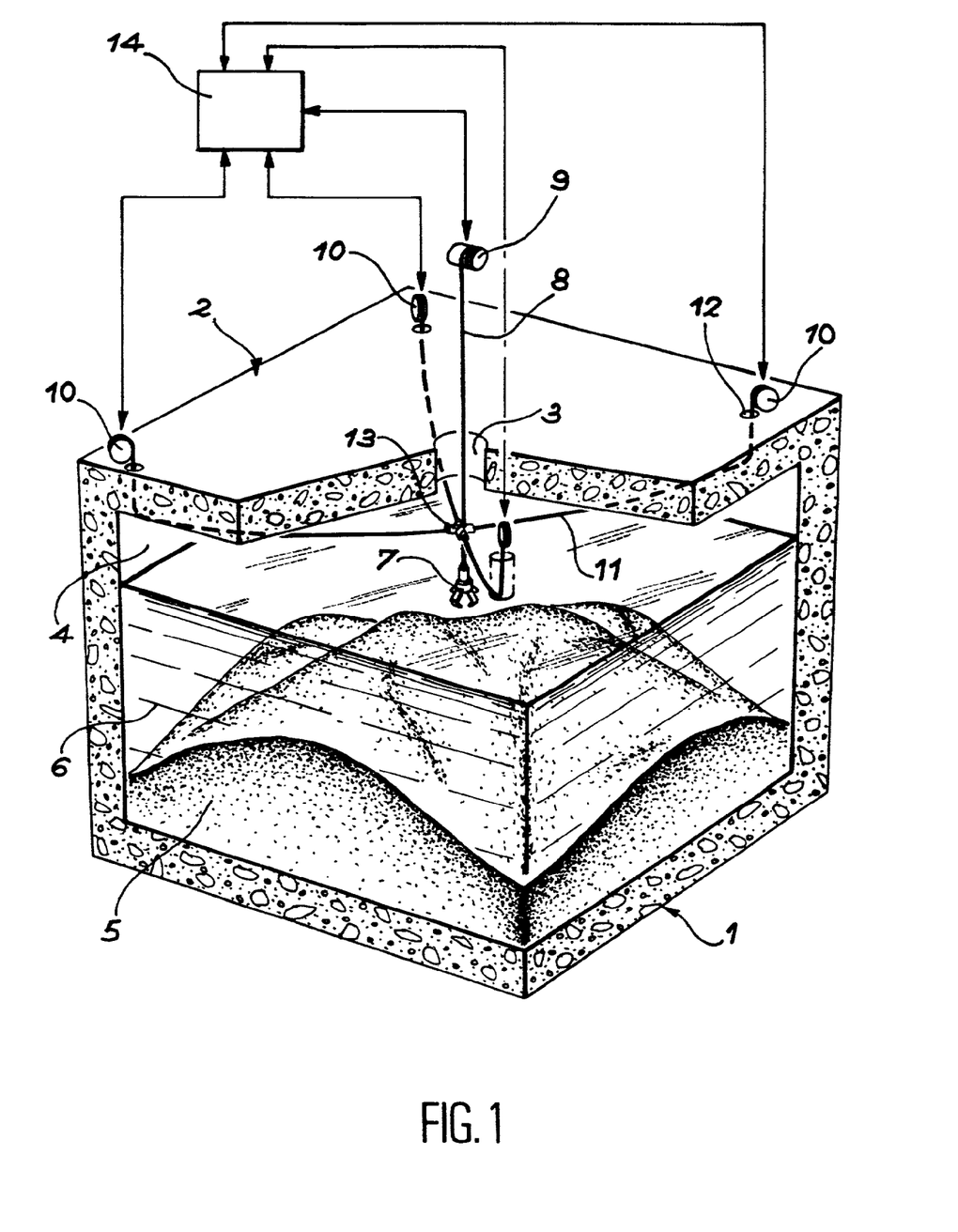
FIG. 1 is a general view of the device and its location.

A silo 1 is made from a cement envelope more or less cubic whose top forms a slab 2 (often called a "cover-slab") where the invention is installed. Slab 2 is pierced by an opening 3 at its centre, which makes to possible to gain access to the pit 4 enclosed by silo 1 and through which waste is tipped. In the most general situation, it is possible to distinguish a pile of solid waste 5 at the bottom of the pit 4 and a layer of liquid waste 6 which is higher than the solid waste; waste of any consistency can evidently be tipped in and left to settle.

The opening 3 serves for introducing a grab 7, intended to take samples of solid waste 5 and which here represents the tool for which the invention is intended, but it is evident that many other tools could replace it according to the nature of the work to be done. The grab 7 is suspended from a support cable 8 rolled on a lifting winch 9. Four guide winches 10 can be noted at the corners of the slab 2, from where the respective guide cables 11 are unrolled, passing under slab 2 after crossing through the drill holes 12. The guide cables 11 converge on a part in the shape of an cut-out crosspiece, here crosspiece 13, on which the support cable 8 slides. A control system 14 is linked to the winches 9 and 10 to give commands: the correct rolling and unrolling of the guide cables 11 makes it possible to move the crosspiece 13 at will under the slab 2, as well as the grab 7 which hangs beneath it; and control of the support cable 8 makes it possible to lower or lift the grab 7, particularly when it overhangs the desired sampling point. The control system 14 comprises a computer linked to the motors and control sensors of the winches 9 and 10; supplementary details about the control procedure will be given below.

Figure 2:
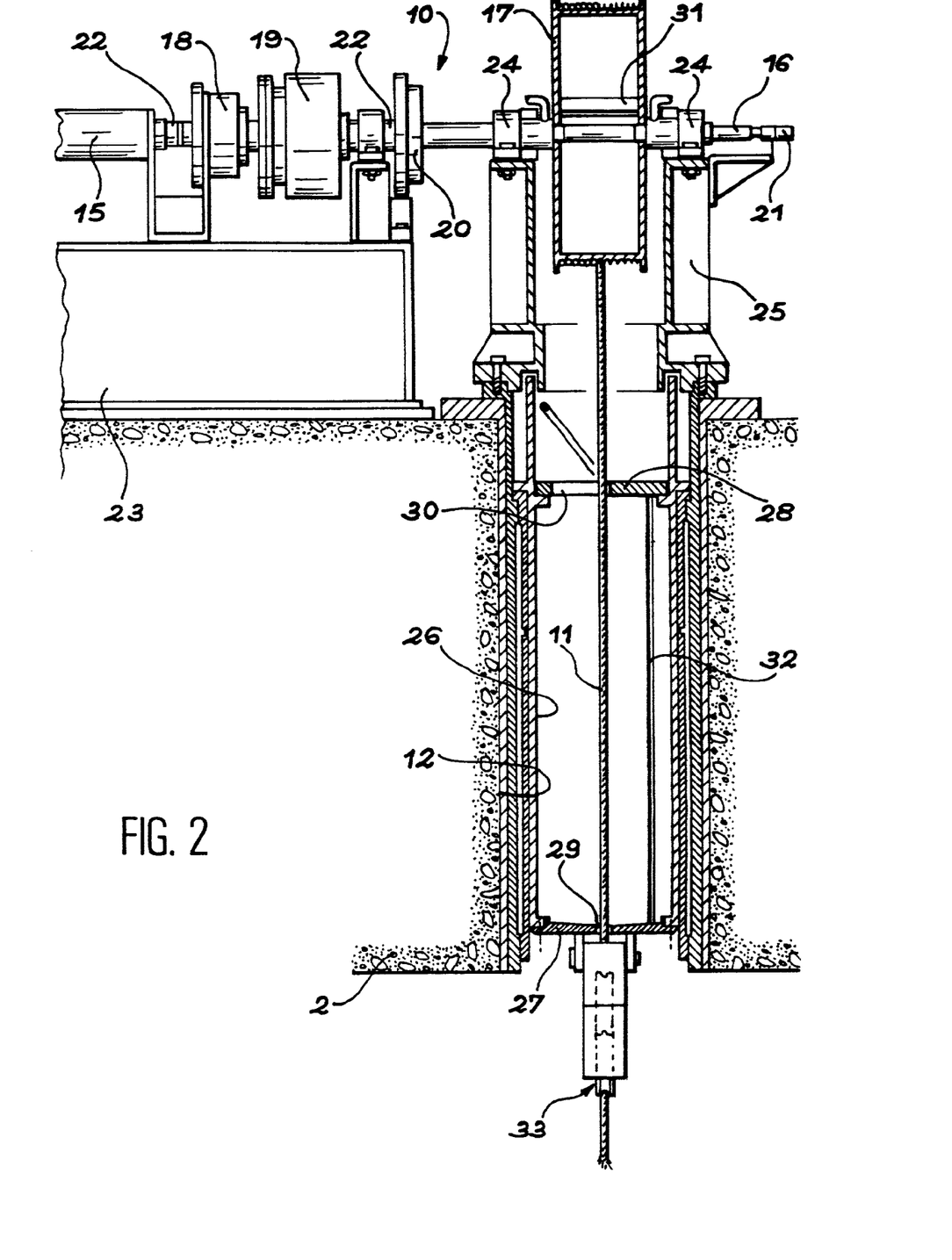
FIGS. 2 and 3 are representations of the drill holes intended for the guide cable and also show adjacent equipment.

FIG. 2 represents a front view of a guide winch 10. Its motor is referenced 15 and drives the horizontal rotation axle 16 of a drum 17 by a kinematic linkage comprising a reducer 18, a torque limiter 19 and a sensor 20 for measuring torque. The aim of the torque limiter 19 is to prevent imposing too high a traction on the guide cable 11 by uncoupling the motor 15 and, if one so wishes, the sensor 20 makes it possible to evaluate the lengthening of the guide cable 11 consecutive to this traction; it is thus linked to the control system 14. Finally, the axle 16 is provided with a resolver 21, or another sensor capable of measuring the rotation angles and thus the rolling and unrolling of the guide cable 11. The motor 15 and its output shaft (coaxial with axle 16) are supported by bearings 22 of a frame 23 fixed on the slab 2, and the rotation axle 16 of the drum 17 is mounted on another pair of bearings 24 of another frame 25, also fixed on the slab 2. The drill hole 12 is equipped with a sleeve 26 whose first function is to re-establish the seal of slab 2 at this point and, for this, comprises a first washer 27 at its lower extremity and a second washer 28 at its upper extremity. Nonetheless the guide cable 11 has to pass through the sleeve 26 and the washers 27 and 28; this is why these two washers are provided with diametral slits 29 and 30, which are arranged in such a way as to cross each other in order to avoid radiation originating from the waste 5 and 6 crossing through the drill hole 12 too easily. Another aim of the slit 30 of the upper washer 28 is to allow the guide cable 11 to pass through without friction, whatsoever the part of the drum 17 from which it has been unrolled: it is thus parallel to the unrolling edge of the drum 17. A crossbar 31, called an anti-run-back, is placed against this unrolling edge so as to apply the guide cable 11 by pressure, for a reason which will be explained below.

The mounting of the guide cable 11 in the sleeve 26 can be accomplished in practice by basing it on a generatrix 32 taking care that the washers 27 and 28 can rotate on it. The edges of the slits 29 and 30 and the generatrix 32 are then aligned before engaging the guide cable 11 in the sleeve 26; next the washers 27 and 28 are turned to cross the slits 29 and 30.

Figure 3:
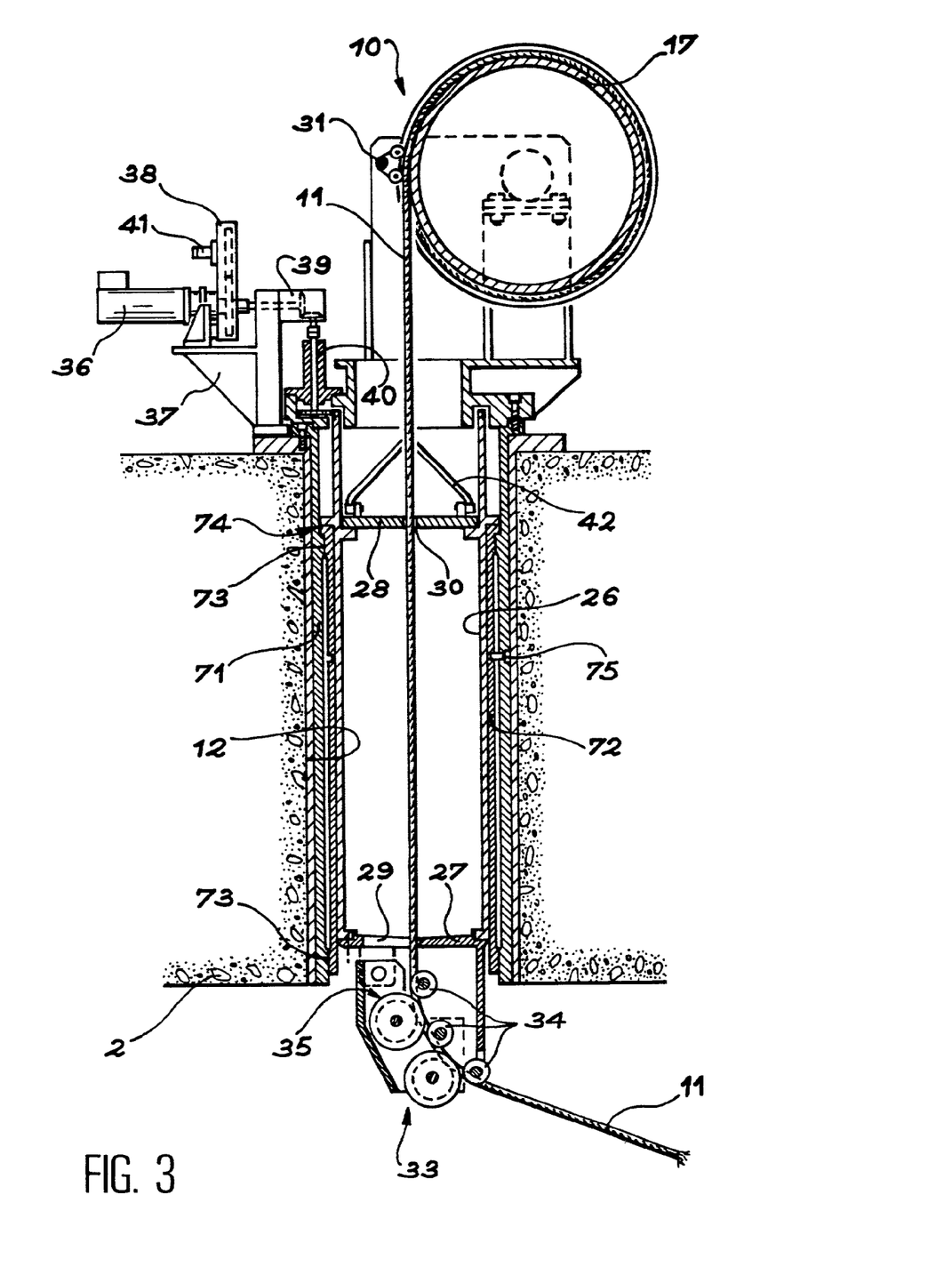

FIG. 3 is a side view of the same parts, but it will serve essentially to illustrate the sleeve 26 in detail.

The lower washer 27 carries a return box 33 composed of rollers 34 in the form of a dual wheel which defines a groove 35 between them and through which the guide cable 11 passes. The groove 35 is curved, with a vertical upper extremity and a horizontal or oblique lower extremity, in order to allow the guide cable 11 to change from a vertical length, where it crosses drill hole 12 to an oblique or horizontal length under the slab 2 where it remains sufficiently high above the level of the liquid waste 6. The return box 33 should be directed towards the crosspiece 13: the sleeve 26 is then set on the slab 2 in such a way as to pivot, and a motor 36, mounted on a frame 37 fixed to the slab 2, drives it by the intermediary of a reducer 38, a pinion 39 and a toothed crown 40 mounted on the periphery of the sleeve 12. An encoder 41 informs the control system 14 of the movements made by the sleeve 26. Reference 42 shows a handle fixed to the upper washer 28 which makes it possible to extract the sleeve 26 from the drill hole 12 or to let it descend. Finally, it is to be noted that the rotating and extractable sleeve 26 is engaged in a fixed sleeve 71 coating the drill hole 12 and that there is an intermediary sleeve 72 slipped between them. This intermediary sleeve 72 pivots inside the fixed sleeve 71 by sliding on a pair of O-rings 73; in addition, there is play between the sleeve 26 and the intermediary sleeve 72. Thus, the return box 33 is made to rotate by the guide cable 11 and this drives the sleeve 26 and the intermediary sleeve 72, which pivots with little friction on the fixed sleeve 71. Stops 74 make it possible to stack the sleeve 26 on the intermediary sleeve 72. Lugs 75 engaged in a circular groove of the fixed sleeve 71 enable it to prevent the intermediary sleeve 72 from falling into the pit 4.

Figure 4:
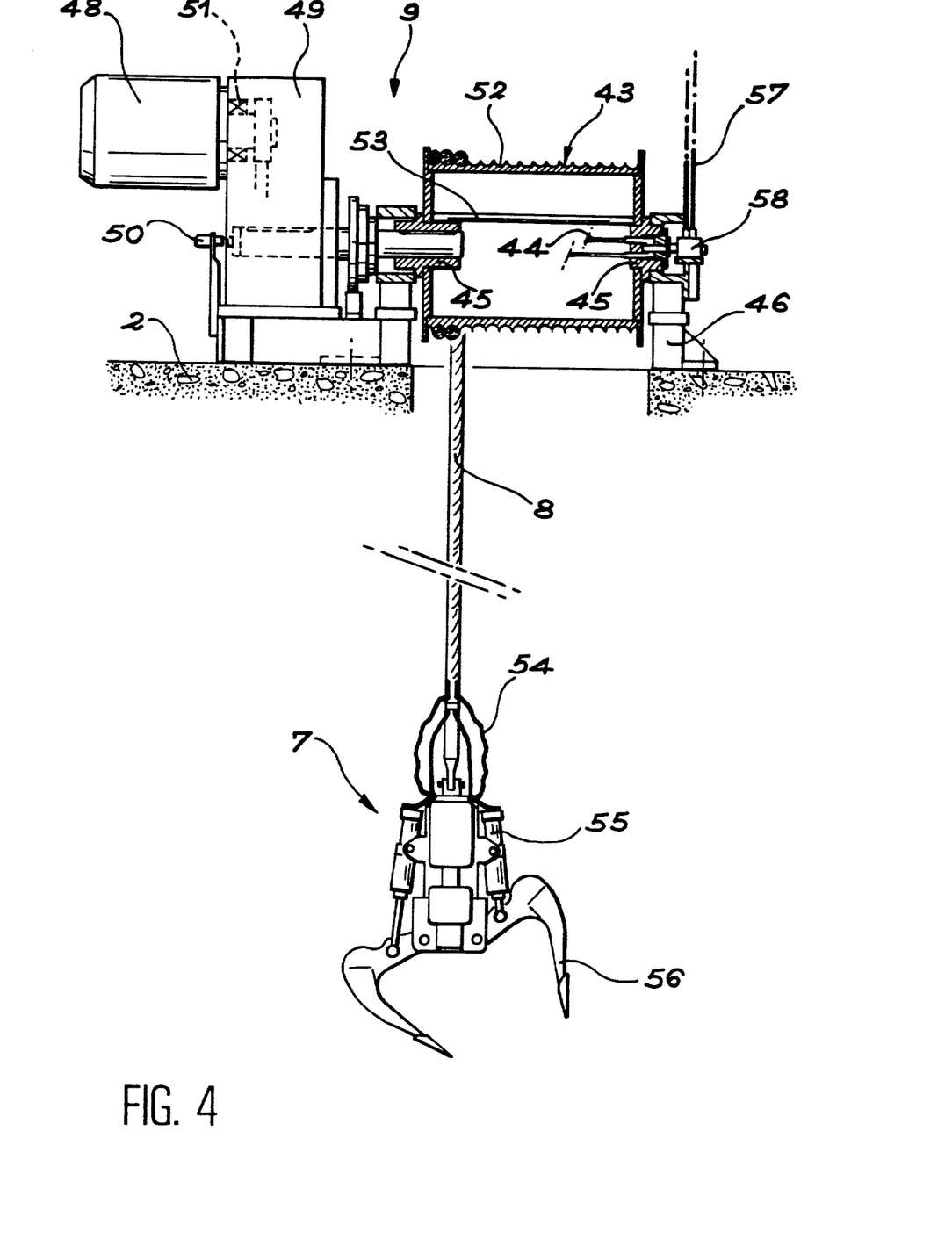
FIG. 4 is a single view of the support cable.

The lifting winch 9 of the support cable 8 is shown in FIG. 4. It also comprises a drum 43 with horizontal rotation axles 44 mounted on a pair of bearings 45 of a frame 46 fixed on the slab 2, and a motor 48 drives through the intermediary of a reducer 49. An encoder 50 makes it possible to measure the rotations of the axle 44 and to transmit this to the control system 14. The motor 48 is also supported by bearings 51, on part of the frame 46.

An essential element of the construction is that the drum 43 has its outside surface notched by a helicoidal groove 52 intended for rolling the support cable 8 in a single layer, which then follows the groove 52 along the drum 43 when it is rolled. An antislip crossbar 53 analogous to that 31 of the guide winches 10 ensures this function by pressing the lifting cable 8 as soon as it approaches the groove 52 and thus forcing it to follow its oblique direction. It is to be noted that such helicoidal grooves already exist but in general their aim is to prevent what is called the build-up (tangling) of a cable unwound at great speed and of great length, in arranging its first layer and then each of the following ones so that they are evenly superposed; cables 8 and 11 are much shorter here and the intended aim is simply to spread them in a single layer so that one turn of the drum 17 or 43 unwinds one determined and unchanging diameter coil of cable.

In this embodiment of the invention, the support cable 8 is unrolled at the same time as a pipe 54 providing fluid to the jacks 55 for displacing the claws 56 of the grab 7. The pipe 54 is linked to a fixed pipe 57 by the intermediary of a rotating joint 58 prolonging the axle 44 and next to the drum 43. The ensemble constituted by the lifting cable 8 and the pipe 54 is more easily subject to damage and more difficult to guide than a single cable, which means that supplementary precautions have to be taken as herein to solve this problem.

Figure 5:
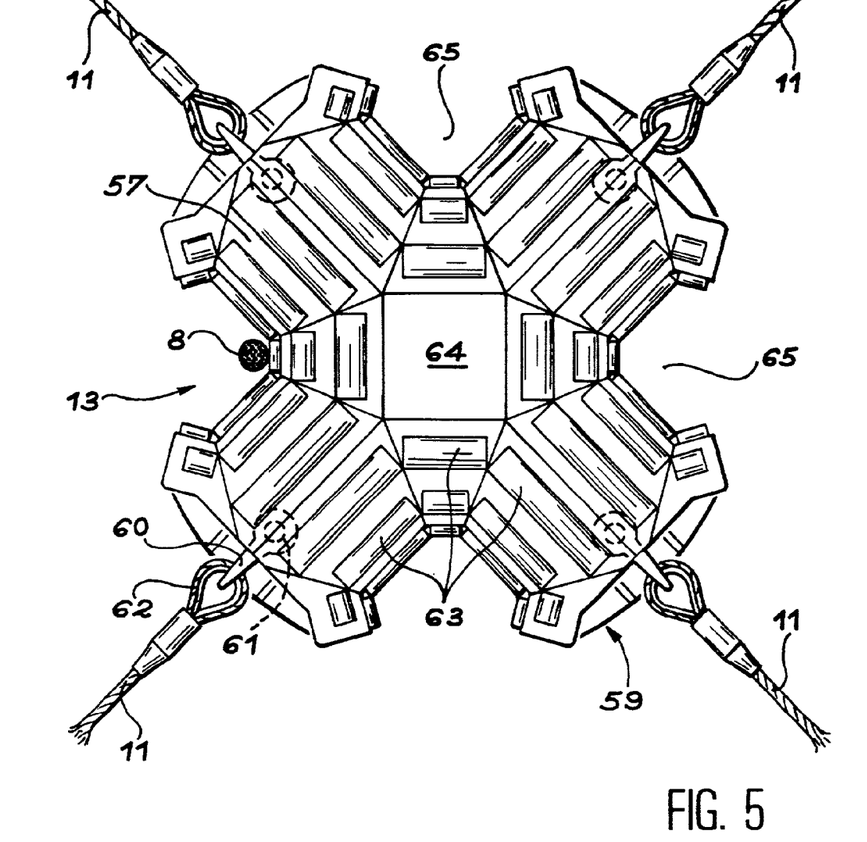
FIGS. 5 and 6 are views of the crosspiece to which the guide cables are hooked.
Figure 6:
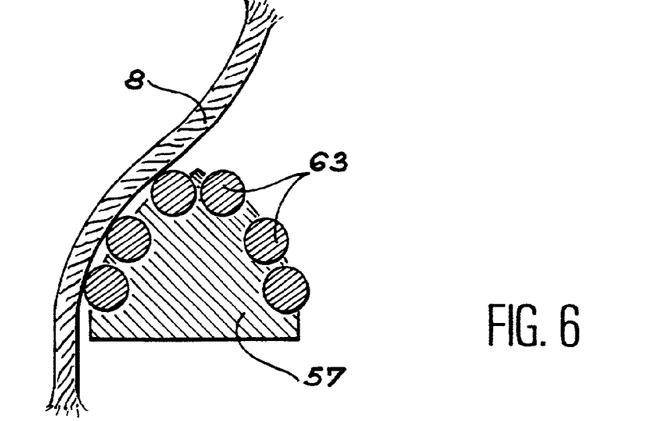

The crosspiece 13 is seen from above in FIG. 5. It is composed of four appendices 59 directed towards the guide cables 11 and terminated by vertical rings 60 pivoting around a vertical axis 61, in which the loops 62 at the ends of the cables 11 are engaged. This mounting makes it possible to direct the crosspiece 13 with high precision. In addition, the appendices 59 are provided with rollers 63 on their upper faces, as well as the body 64 of the crosspiece 13 which unites the appendices 59 together. These faces are convex so that the support cable 8 rests on the rollers 63 along a suitable length, as FIG. 6 shown as a cross-section through one of the arms 59 makes perfectly clear; in addition, care has to be taken to shape these sliding surfaces of the support cable 8 with concavities between appendices 59 adjacent to the hooking of the guide cables 11, in such a way that the support cable 8 in encouraged to enter into the bottom of one of the grooves 65 thus formed and to remain there even when there are oscillations: it is then placed with high precision on the crosspiece 13 and slides without excessive friction.

Figure 7:
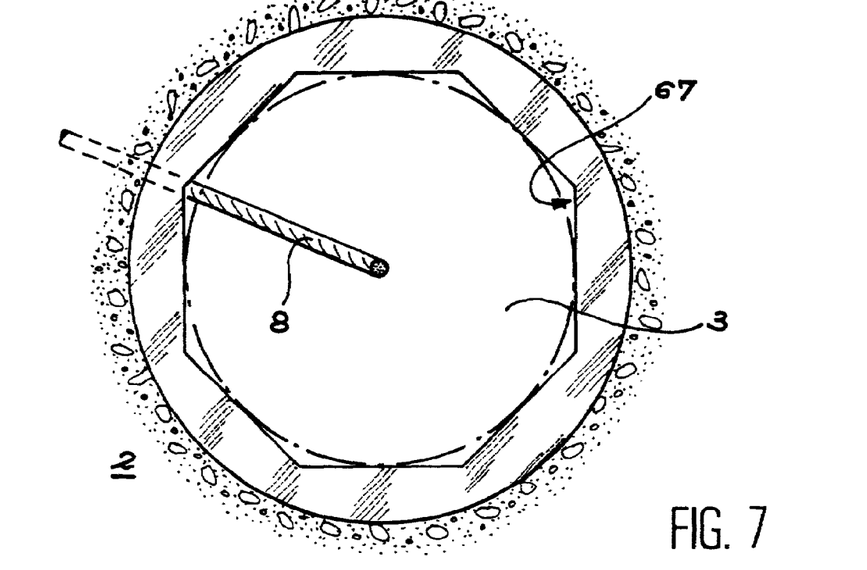
FIGS. 7 and 8 are views of the opening in the slab, FIG.
Figure 8:
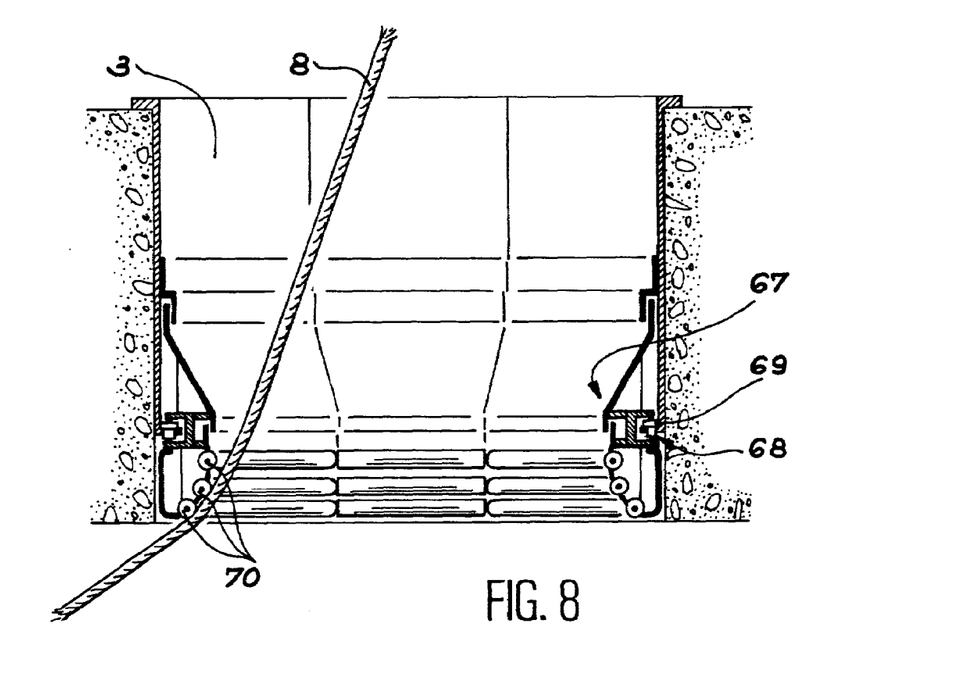
Figure 9:
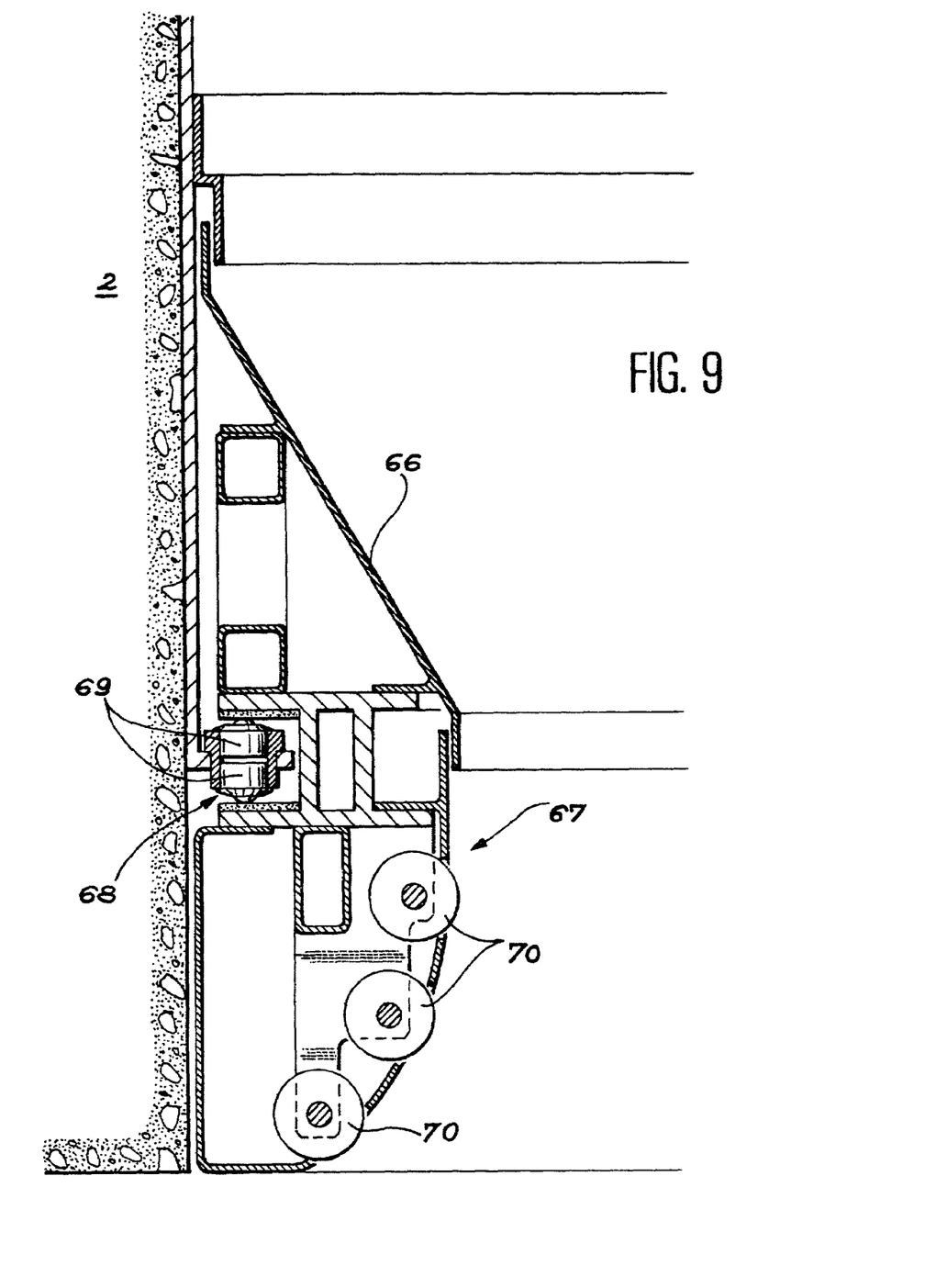
FIG. 9 is an enlargement of FIG. 8.

Finally there is the description of FIGS. 7 to 9 which represent the trimming of the opening 3 of the slab 2. Normally a cement cover closes the opening 3 but it is withdrawn when the invention is to be used. Then one can see an octagonal crown 67 appear, which encircles the opening 3. This crown 67 turns on a circular bearing surface 68 of the slab 2 provided with two ball bearing circles 69 directed upwards and downwards and which support the crown 67 by keeping it at a constant level, eventually preventing it being lifted when the support cable 8 under tension passes under it, and the sides of the octagon are defined by groups of rollers 70 superposed in receding positions towards the bottom, so that they are further and further from the centre of the opening 3. If the grab 7 has to be directed towards the sides of the pit 4, the support cable 8 is pulled towards the crown 67 until it touches the rollers 70 on one of its sides; it then slides along them easily and without friction with the slab 2; the crown 67 rotates to reduce friction with the support cable 8 and wear of the latter. Generally, the support cable 8 slides up to the angle of two sets of neighbouring rollers 70 and remains there until the end of the procedure, consequently controlling the rotations of the crown 67 to follow its movements: the friction of the support cable 8, which would have been significant if it had slid against the periphery of the opening and would have hindered correct unrolling, thus becomes very slight. Reference 66 defines a funnel covering the crown 67 and the bearing surface 68 and protects them against runoff.

The operation of the device can be described fairly simply: once it has been decided to take the grab 7 to a defined point in the pit 4, it is lowered slightly through the opening 3 after having placed the crosspiece 13 not far from it, in such a way that the support cable 8 passes in front of the groove 65 which is directed towards the position to be reached. Then certain guide cables 11 are rolled up while others are unrolled to displace the crosspiece 13 in such a way as to place the support cable 8 in the chosen groove 65 and then to move the grab 7 towards the chosen position; these movements are accompanied by progressive unrolling of the support cable 8 to prevent the grab 7 rising up to the crosspiece 13; the control system 14 constantly calculates the length of each of the guide cables 11 thanks to the information from the resolvers 21, then the position of the crosspiece 13 and that of the grab 7; it also orients the sleeves 26. It can take into account the lengthening of the guide cables 11 consecutive to their traction and of the position of the groove 65 on which the lifting cable 8 slides, to improve the calculation of the position of the grab 7. It takes care not to apply excessive force on the guide cables 11; however the torque limiters 19 make it possible to avoid excessive traction and to relax the cables 11 until the traction has disappeared. When the grab 7 overhangs the position required, the control system 14 continues to actuate the lifting winch 9 until the grab 7 has been lowered to the height required; it takes into account the length of support cable 8 which has already been unrolled and which has been indicated by the encoder 50. The jacks 55 can then be put into action to close the claws 56 and seize a sample of the waste, after which the preceding operations are repeated in reverse to bring the grab 7 back underneath the opening 3 and to lift it up.

What is claimed is:

1. A device for examination, sampling or extraction of the contents of a silo (1) located under a slab (2) pierced by an opening (3), by an organ suspended from a support cable (8) and lowered through the opening (3), comprising at least three guide cables (11) located under the slab (2), converging towards a guide means (13) to which they are hooked at hooking points by crossing the slab (2) by drill holes (12) arranged in a crown and rolled on winches (10) driven by motors, a common control system (14) for the winches (10, 9), the guide means being provided at a periphery thereof with concavities (65) for the support cable which alternate with the hooking points (60) of the guide cables (11), the concavities (65) of the guide means being defined by at least one sliding surface (63) and being concave when linking the hooking points (60) of the guide cables.

2. A device according to claim 1, characterised in that the motors (15) of the winches (10) are provided with force limiters (19).

3. A device according to claim 1, characterised in that the motors of the winches are provided with force measurement sensors (21) linked to the control system (14).

4. A device according to claim 1, characterised in that the support cable (8) is rolled onto a winch (9) driven by a motor (48) directed by the control system (14).

5. A device according to claim 1, characterised in that the drill holes (12) are provided with a sleeve (26) provided with a washer (27) with an opening (29) for the passage of a respective guide cable (11).

6. A device according to claim 5, characterised in that the washer (27) carries rollers (33, 34) defining a guide groove of a respective guide cable (11).

7. A device according to claim 6, characterised in that the groove is curved and comprises a vertical extremity towards the washer (27) and an oblique extremity directed towards the guide means (13).

8. A device according to claim 7, characterised in that the sleeves (26) are mounted on the slab so as to pivot, and are driven by motors (36) directed by the control system.

9. A device according to claim 5, characterised in that the sleeves comprise a second washer (28) with an opening for the passage of a guide cable, the openings (29, 30) of the washers being crossed slits.

10. A device according to claim 1, characterised in that the winches (9, 10) comprise drums (17, 43) with a surface cut out with a helicoidal groove (52) for reception of the cables (8, 11) in a single rolled layer.

11. A device according to claim 10, characterised in that the winches comprise crossbars (31, 53) for pressing on the guide cables, set against the drums.

12. A device according to claim 1, characterised in that the guide cables are four and the drill holes (12) are arranged in a rectangle.

13. A device according to claim 1, characterised in that the guide cables are hooked to a guide means by engagement of an loop (62) in a ring (60).

14. A device according to claim 1, characterised in that the sliding surfaces (63) of the guide means (13) are provided with rollers (63) and are convex in the vertical direction.

15. A device according to claim 1, characterised in that the opening of the slab is provided with a crown (67) of rollers (70).

16. A device according to claim 15, characterised in that the crown of rollers is polygonal and mounted on the opening (3) of the slab (2) in such a way as to turn freely.

17. A device according to claim 16, characterised in that the crown of rollers is receding downwards and mounted on the opening of the slab with upward and downward supports (69).

* * * * *

UNITED STATES PATENT AND TRADEMARK OFFICE
CERTIFICATE OF CORRECTION

PATENT NO. : 6,951,442 B2  Page 1 of 1
DATED : October 4, 2005
INVENTOR(S) : Guyot et al.

It is certified that error appears in the above-identified patent and that said Letters Patent is hereby corrected as shown below:

<u>Title page,</u>
Item [75], Inventors, delete "Bruno Julienne" and insert -- Bruno Jullienne --.

<u>Column 2,</u>
Line 34, delete "FIG. FIG. 9" and insert -- Fig. 9 --.

Signed and Sealed this

Twenty-eighth Day of March, 2006

JON W. DUDAS
*Director of the United States Patent and Trademark Office*